(12) United States Patent
Tal

(10) Patent No.: US 7,476,200 B2
(45) Date of Patent: Jan. 13, 2009

(54) DEVICE AND METHOD FOR REGULATING BLOOD FLOW

(76) Inventor: Yair Tal, 81 Habsor St., Shoham (IL) 73142

( * ) Notice: Subject to any disclaimer, the term of this patent is extended or adjusted under 35 U.S.C. 154(b) by 0 days.

(21) Appl. No.: 10/546,197

(22) PCT Filed: Feb. 19, 2004

(86) PCT No.: PCT/IL2004/000166

§ 371 (c)(1),
(2), (4) Date: May 4, 2006

(87) PCT Pub. No.: WO2004/073796

PCT Pub. Date: Sep. 2, 2004

(65) Prior Publication Data

US 2006/0206029 A1 Sep. 14, 2006

(30) Foreign Application Priority Data

Feb. 19, 2003 (IL) .................................... 154531

(51) Int. Cl.
*A61B 5/02* (2006.01)
(52) U.S. Cl. .................................................. 600/485
(58) Field of Classification Search ................. 600/16, 600/481–507; 604/601
See application file for complete search history.

(56) References Cited

U.S. PATENT DOCUMENTS 4,995,857 A * 2/1991 Arnold ........................ 600/16

5,129,394 A 7/1992 Mehra
5,267,490 A * 12/1993 Howells .................. 73/863.52

(Continued)

FOREIGN PATENT DOCUMENTS

WO 01/72239 A2 10/2001
WO 02/26140 A1 4/2002

*Primary Examiner*—Robert L Nasser
*Assistant Examiner*—Karen E Toth
(74) *Attorney, Agent, or Firm*—The Nath Law Group; Jerald L. Meyer; Stanley N. Protigal

(57) ABSTRACT

A system and method for regulating blood flow rate or blood pressure in a second blood vessel or heart chamber to achieve a balanced flow rate or blood pressure between the second blood vessel or heart chamber and a first blood vessel or heart chamber, wherein the first and the second blood vessels and heart chambers are on opposite sides of the circulatory system. The system comprises a monitor that monitors parameters indicative of a difference between the flow rates or blood pressures of the first and the second blood vessels or heart chambers. A regulator regulates the blood flow rate or blood pressure in at least a portion of the second blood vessel or heart chamber. A controller is configured to receive a signal from the monitor and to determine a difference between the flow rate or blood pressure of the first blood vessel or heart chamber and the flow rate or blood pressure of the second blood vessel or heart chamber. The controller determines a second blood flow rate or blood pressure in the second blood vessel or heart chamber that generates the balanced flow rate or blood pressure between the first and the second blood vessels or heart chambers. The controller then signals the regulator to generate the second determined blood flow rate or blood pressure in the at least portion of the lumen of the second blood vessel or heart chamber.

18 Claims, 3 Drawing Sheets

U.S. PATENT DOCUMENTS

| | | |
|---|---|---|
| 5,509,888 A | 4/1996 | Miller |
| 6,010,470 A | 1/2000 | Albery et al. |
| 6,071,258 A * | 6/2000 | Dalke et al. ................ 604/5.01 |
| 6,086,527 A | 7/2000 | Talpade |
| 6,139,487 A * | 10/2000 | Siess ........................... 600/16 |
| 6,141,590 A | 10/2000 | Renirie et al. |
| 6,231,551 B1 | 5/2001 | Barbut |
| 6,275,727 B1 | 8/2001 | Hopper et al. |
| 6,280,377 B1 | 8/2001 | Talpade |
| 6,422,990 B1 | 7/2002 | Prem |
| 6,473,647 B1 | 10/2002 | Bradley |
| 6,507,756 B1 | 1/2003 | Heynen et al. |
| 6,540,658 B1 * | 4/2003 | Fasciano et al. ............... 600/17 |
| 6,669,624 B2 * | 12/2003 | Frazier ....................... 600/18 |
| 6,808,482 B1 * | 10/2004 | Pacella et al. ................. 600/16 |
| 2001/0004675 A1 * | 6/2001 | Woodard et al. .............. 600/16 |
| 2002/0173742 A1 | 11/2002 | Keren et al. |
| 2003/0069465 A1 * | 4/2003 | Benkowski et al. ........... 600/16 |
| 2004/0111006 A1 * | 6/2004 | Alferness et al. .............. 600/16 |
| 2004/0116768 A1 * | 6/2004 | Bolling et al. ................ 600/16 |
| 2004/0236172 A1 * | 11/2004 | Bolling et al. ................ 600/16 |
| 2005/0148925 A1 * | 7/2005 | Rottenberg et al. ............. 604/9 |
| 2005/0159639 A1 * | 7/2005 | Skliar et al. .................. 600/16 |
| 2005/0230314 A1 * | 10/2005 | Kim et al. ................... 210/646 |

* cited by examiner

DEVICE AND METHOD FOR REGULATING BLOOD FLOW

FIELD OF THE INVENTION

This present invention relates to methods and systems for regulation blood flow or pressure.

BACKGROUND OF THE INVENTION

Congestive heart failure (CHF) is a common heart disease, which is recognized as the most common cause of hospitalization and mortality in Western society. CHF is an extremely serious affliction that has a great impact on the quality of life. CHF develops generally in the course of months or years, and can be the end stage of chronic hypertension, infarction, angina, or diabetes. The prevalence of incidents of congestive heart failure has recently increased, and there is considerable morbidity and mortality-associated with its diagnosis. In fact, congestive heart failure is an extremely lethal disease with an estimated five-year mortality for a vast majority of both men and women who encounter the disease.

Congestive heart failure refers to a situation in which the ventricle pumps less blood than a healthy ventricle under the same conditions. The rate at which blood is delivered to the left or right atrium thus exceeds the rate at which blood is pumped out of the heart by the left or right ventricle, respectively.

Congestive heart failure is primarily characterized by ventricular dysfunction. The decreased contractility of the left ventricle leads to reduced cardiac output with consequent systemic arterial and venous vasoconstriction. Ventricular diastolic dysfunction is the inability of the ventricle walls to expand and to fill the ventricle with the same blood volume as a healthy ventricle under the same conditions. Ventricular systolic dysfunction is the inability of the ventricle to contract and push the same blood volume as a healthy ventricle under the same conditions.

Another cause of congestive heart failure is mitral valve dysfunction. The cause of mitral valve dysfunction are mitral insufficiency, mitral stenosis or a combination of these. Mitral insufficiency means that the valve does not completely close. Mitral stenosis means that the valve does not open enough to enable the desired blood flow into the left ventricle.

One consequence of CHF is pulmonary edema, in which fluid accumulates in the lungs due to a higher blood flow rate in the pulmonary arteries than in the pulmonary veins. As pressure in the pulmonary veins rises, fluid is pushed into the air spaces (alveoli). This fluid then becomes a barrier to normal gas exchange in the alveoli, resulting in shortness of breath. This sequence of events results in hypoxemia, hypercapnia, and death.

Dyspnea in patients with CHF appears often at night when the patient is lying and the venous return is increased. This nocturnal dyspnea endangers the patient. Usually is alleviated when the patient sits or stands up.

Presently available treatments for CHF fall into three generally categories: (1) pharmacological, e.g., diuretics; (2) assist systems, e.g., pumps; (3) surgical treatments; and (4) resynchronization.

With respect to pharmacological treatments, diuretics have been used to reduce the workload of the heart by reducing blood volume. While drug treatment improves quality of life, it has little effect on survival. Current pharmacological treatment includes a combination of diuretics, vasodilators, inotropes, beta-blockers, and Angiotensin Converting Enzyme (ACE) inhibitors. The effect is a decrease of symptoms, and improved quality of life, but little change in mortality.

Cardiac assist devices used to treat CHF include, for example, mechanical pumps. Mechanical pumps reduce the load on the heart by performing all or part of the pumping function normally done by the heart. Currently, mechanical pumps are used to sustain the patient until a donor heart for transplantation becomes available for the patient. There are also a number of pacing devices used to treat CHF.

There are at least three surgical procedures for treatment of heart failure: 1) heart transplant; 2) dynamic cardiomyoplasty; and 3) left ventriculectomy. Heart transplantation has serious limitations including restricted availability of organs and the adverse effects of immunosuppressive therapies required following heart transplantation. Cardiomyoplasty includes wrapping the heart with skeletal muscle and electrically stimulating the muscle to contract synchronously with the heart in order to help the pumping function of the heart. Left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

Finally, cardiac resynchronization therapy can be delivered by a cardiac rhythm management device in accordance with a bradycardia pacing mode so that the selected heart chambers are both resynchronized and paced simultaneously.

U.S. Published Patent Application No. 2002/0173742 to Keren et al. describes a shunt for decreasing pressure in a portion of the left ventricle of a patient. The shunt is implanted whereby a volume of blood is released that is sufficient to reduce end diastolic pressure in the left ventricle.

U.S. Pat. No. 5,509,888 to Miller describes a device for regulating fluid flow within a body tube such as a blood vessel. The device includes a ring that is positioned around the body tube. The caliber of the ring is under the control of a programmable control unit. Decreasing the caliber of the ring constricts the body tube thus decreasing the flow of fluid in the body tube.

WO 01/72239 describes an implant adapted for insertion into blood vessels for reducing the diameter of a blood vessel. The implant is used, for example, in a coronary sinus or other coronary vein to reduce the flow rate of blood in the vessel.

U.S. Pat. Nos. 6,280,377 and 6,086,527 to Talpade describe a system for regulating blood flow to a portion of the vasculature, such as the renal system, in order to treat heart disease. Blood flow in the portion of the vasculature is regulated so as to control physiological feedback responses to high or low blood pressure, in order to relieve overload conditions on the heart. Increasing blood flow to the renal arteries thus inhibiting the renal response to hypotension and inhibiting the vascorestriction and increased blood volume associated with that response. This reduces the overload and stress on the heart, thus allowing passive rehabilitation of the myocardial system.

U.S. Pat. No. 6,473,647 to Bradley describes an implantable cardiac stimulation device that monitors progression or regression in a patient's heart disease. A pulse generator delivers pacing pulses to the heart to cause responses of the heart. A sensing circuit senses the responses of the heart and generates response signals. A processor is programmed to analyze the response signals, to isolate a given characteristic of the response signals and to quantify the isolated characteristics to provide corresponding quantized values. Relative changes in the quantized values over time are indicative of the progression or regression in the patient's heart disease. A memory stores the quantized values and a telemetry circuit transmits the stored quantized values to an external receiver for analysis.

U.S. Pat. No. 6,507,756 to Heynen et al describes rate responsive pacing systems that employ a time-dependent atrial-ventricular (AV) delay. A starting or initial AV delay is set to an intrinsic AV delay time interval exhibited by the patient's heart at the time of implant. A chronic AV delay is then set to a therapeutic AV delay time interval that is shorter than the intrinsic AV delay time interval. A Time-Adaptive AV delay (TA-AV delay) is employed during a post-implant Time-Adaptive period that gradually changes the initial AV delay to the chronic AV delay at the end of the post-implant Time-Adaptive period.

U.S. Pat. No. 6,275,727 to Hopper et al describes a method and apparatus for providing congestive heart failure therapy status. An electronic device, preferably a cardiac rhythm management device, capable of measuring transthoracic impedance and for sensing a level of physical activity is implanted in a patient. The transthoracic impedance signal is processed to obtain an estimate of the subject's minute ventilation, respiratory rate and tidal volume. From accelerometer measured activity, an estimate is obtained of oxygen uptake and carbon dioxide production. Ratios of tidal volume to respiratory rate, tidal volume to inspiratory time, minute ventilation to carbon dioxide production and oxygen uptake to heart rate are meaningful status indicators for assessing the efficacy of particular therapy regimens to CHF patients.

U.S. Pat. No. 6,422,990 to Prem describes a method and apparatus for use with a blood pump. Multiple sensors are positioned around the ventricle. Based on the measurements of the sensors it is possible to calculate either a cross sectional area or a volume of the ventricle during distension and contraction. The calculated area or volume is indicative of distension and contraction than a single radial dimension measurement. The area or volume can be utilized to control the blood pump flow rate to avoid overly distending or contracting the ventricle and for operating the flow rate in a pulsatile manner to closely approximate the natural pumping action of the heart.

SUMMARY OF THE INVENTION

The present invention provides a system and a method for matching the blood flow rate or blood pressure in a blood vessel to the blood flow rate or blood pressure in another blood vessel. The invention may be used, for example, to balance the blood flow rate into the left atrium to the blood flow rate out of the right ventricle. Alternatively, the invention may be used to balance the blood flow rate into the right atrium to the blood flow rate out of the left ventricle. The invention may also be used to balance the blood flow rate into the lungs to the blood flow rate out of the lungs. The invention may thus be used for the treatment of CHF or pulmonary edema.

In accordance with the invention, the system comprises a monitor that generates a signal indicative of the blood flow rate or the blood pressure in a first blood vessel or heart chamber (e.g. a pulmonary vein or left atrium). The system further comprises a device referred to herein as a "regulator". The regulator is configured to be positioned in or adjacent to a second blood vessel (e.g. the inferior or superior vena cava or the right atrium or the pulmonary artery), and to regulate the blood flow rate or blood pressure in at least a region of the second blood vessel or heart chamber. The regulator may have, for example, a variable conformation, and different conformations of the regulator generate a different cross-sectional area of the second blood vessel lumen in at least a region adjacent to the regulator. Alternatively, the regulator may be a cardiac assist device that regulates the flow of blood in a heart chamber by applying electrical pulses to the chamber wall. The signal generated by the monitor is input to a controller. The controller includes a processor that determines from the input signal a blood flow rate or blood pressure in the first blood vessel or heart chamber. The processor then determines the blood pressure in the second vessel or heart chamber that would yield a desired blood flow rate or blood pressure in the first vessel or chamber. The controller then outputs a signal to the regulator, in response to which the regulator generates the determined blood pressure in the second vessel or chamber.

In one embodiment, the regulator includes an inflatable balloon that is positioned in the lumen of the second vessel or heart chamber. A compressor delivers a fluid such as air to the balloon and inflates the balloon so as to obstruct a portion of the second blood vessel or heart chamber so as to achieve the determined blood flow rate or blood pressure in the second vessel or heart chamber.

In a second embodiment, the regulator includes a ring that is positioned around the second vessel or heart chamber and that is capable of constricting the second vessel or heart chamber to achieve the determined cross-sectional area of the second vessel.

In a third embodiment, the regulator comprises a mechanical valve having one or more partially closed conformations. The regulator is configured to be installed inside a blood vessel or heart chamber and to be secured to the walls of the blood vessel or heart chamber. When in a partially closed conformation, the cross-sectional area of the lumen of the blood vessel or heart chamber is decreased.

In a fourth embodiment, the regulator comprises one or more electrodes configured to be attached to the walls of a blood vessel and to stimulate the muscles of a blood vessel wall to contract so as to decrease the cross-sectional area of the lumen of the blood vessel.

In a fifth embodiment, the regulator comprises one or more electrodes configured to be attached to a wall of a heart and to stimulate heart wall muscles to regulate pacing of the muscles so as to decrease the discharge rate of blood from a heart chamber.

In a sixth embodiment, the regulator comprises one or more electrodes configured to be attached to skeletal muscles surrounding veins and to stimulate the muscles to contract so as to decrease the cross-sectional area of the lumen of the veins.

In a seventh embodiment, the regulator comprises a ring or hoop configured to be tightened around one or two legs to decrease the cross-sectional area of the lumen of the femoral veins.

In an eighth embodiment, the regulator comprises a ring or hoop configured to be tightened around the waist to decrease the cross-sectional area of the lumen of the inferior vena cava or the common iliac veins.

In a ninth embodiment, the regulator is a controlled cardiac assist device, which is applied to the systemic circulation to assist a diseased. left chamber to pump blood to the body tissues. The monitor comprises a strain gage, which is applied to the interatrial septum.

The monitor may monitor any phenomenon known to be correlated with blood flow rate or blood pressure. For example, the monitor may detect displacements in a blood vessel or heart chamber wall, a pressure gradient across the interatrial septum, blood flow rate, blood pressure, a pressure difference between left and right atria; deflections of the inter ventricular septum; a blood oxygen saturation level; deflections of the interatrial septum; a blood enzyme level; transthoracic or intrathoracic electrical impedance; temperature or sound, all as is known in the art. Those measurements can, as a non-limiting example, be measured in the coronary vessels. When the strain gage detects a deflection of the septum from the left to the right atrium, the output of the regulator is increased. Alternatively, when the strain gauge detects a deflection of the septum from the right to the left atrium, the output of the regulator is decreased.

The monitor or the regulator may be positioned on or near any blood vessel or heart chamber, for example:
i) a pulmonary vein;
ii) a pulmonary artery;
iii) a superior vena cava
iv) an inferior vena cava;
v) a femoral vein or artery;
vi) an iliac vein or artery;
vii) a renal vein or artery;
viii) a subclavian vein or artery;
ix) the right of left carotid artery;
x) a jugular vein;
xi) a coronary vein or artery;
xii) a right atrium;
xiii) a left atrium;
xiv) a right ventricle; and
xv) a left ventricle.

The monitor may be any known device for measuring blood flow rate or blood pressure. For example, a strain gauge may be affixed to the first vessel, or to the interatrial septum of the heart. The strain gauge produces an electronic signal indicative of the ambient blood pressure. Blood pressure or blood flow rate can also be determined by measuring blood acceleration, measuring electrical inductance, impedance or capacitance of the blood, blood acceleration, optical imaging, optical spectral analysis, light transmittance, temperature measurements (e.g. by a thermostat, thermistor or thermocouple), acoustic transduction and by ultrasound or Doppler measurements of the blood in the first blood vessel.

The monitor may monitor the level and the severity of CHF by any known device and method including the known ones. Non-limiting examples of such devices are:
i) a strain gauge;
ii) an accelerometer;
iii) a device for measuring electrical impedance;
iv) a device for measuring electrical inductance;
v) a device for measuring capacitance;
vi) a device for optical imaging of a blood vessel;
vii) a device for spectral analysis;
viii) a device for measuring light transmittance of blood;
ix) a thermistor;
x) a thermocouple;
xi) a thermostat;
xii) an acoustic transducer;
xiii) an ultrasound transducer; and
xiv) a device for Doppler measurements of blood.

The system may optionally include a remote control to allow programming of the processor, calibration of the system or enable the user to override the automatic mode of operation of the system. The remote control unit may include a display panel showing the values of the measurements performed by the system and other data regarding the system itself, for example a reminder to replace or load the batteries of the control unit, etc.

The system may optionally include an alarming sensor applied to a third blood vessel that measures one or more blood flow parameters. If the sensor detects that the system has produced in the third vessel an inappropriate value of the measured blood flow parameter or parameters, it may signal the controller through a third channel to bring the regulator to a state that allows maximum blood flow in the circulatory system.

The term "same side" when referring to the circulatory system means that both the monitor and the regulator are located in blood vessels both of which carry either oxygenated blood or deoxygenated blood.

The term "opposite sides" when referring to the circulatory system means that the monitor or the regulator are located in blood vessels one of which carries oxygenated blood while the other carries deoxygenated blood. Thus, the first blood vessel or heart chamber and the second blood vessel or heart chamber may be positioned either on the same side or on opposite sides of the circulatory system.

In its first aspect, the invention thus provides a system for regulating blood flow rate or blood pressure in a second blood vessel or heart chamber to achieve a desired blood flow rate or a blood pressure in a first blood vessel or heart chamber, comprising:
i) a monitor monitoring blood flow rate or blood pressure in the first blood vessel or heart chamber;
ii) a regulator regulating a blood flow rate or blood pressure in at least a portion of the second blood vessel or heart chamber; and
iii) a controller configured to:
  receive a signal from the monitor indicative of a blood flow rate or blood pressure in the first blood vessel or heart chamber;
  determine a first blood flow rate or the blood pressure in the first blood vessel or heart chamber from the signal;
  determine a second blood flow rate or blood pressure in the second blood vessel or heart chamber that generates the desired blood flow rate or blood pressure in the first blood vessel or heart chamber; and
  signal the regulator to generate the second determined blood flow rate or blood pressure in the at least portion of the lumen of the second blood vessel or heart chamber.

In its second aspect, the invention further provides a method for regulating blood flow rate or blood pressure in a second blood vessel or heart chamber to achieve a desired blood flow rate or a blood pressure in a first blood vessel or heart chamber, comprising:
i) monitoring blood flow rate or blood pressure in the first blood vessel or heart chamber; and
ii) regulating a blood flow rate or blood pressure in at least a portion of the second blood vessel or heart chamber
iii) receiving a signal from a monitor indicative of a blood flow rate or blood or blood pressure in the first blood vessel or heart chamber;
iv) determining the first blood flow rate or blood pressure in the first blood vessel or heart chamber from the signal;
v) determining a second blood flow rate or blood pressure in the second blood vessel or heart chamber that generates the desired blood flow rate or blood pressure in the first blood vessel or heart chamber; and
  signaling the regulator to generate the second determined blood flow rate or blood pressure in at least a portion of the lumen of the second blood vessel or heart chamber.

In a third aspect, the invention thus provides method for deploying a sensor in a coronary vessel by catheter means comprising attaching the sensor to a catheter and delivering the sensor to the coronary vessel.

In a fourth aspect, the invention further provides a system for deploying a sensor in a coronary vessel, comprising a catheter configured at an end to reversibly grasp the sensor.

In a fifth aspect, the invention thus provides a method for deploying a sensor on a heart wall comprising locating the sensor to a catheter and delivering the sensor through a coronary vessel to the heart wall.

In a sixth aspect, the invention further provides a system for deploying a sensor on a heart wall comprising a sensor located to a catheter and delivered through a coronary vessel to the heart wall.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
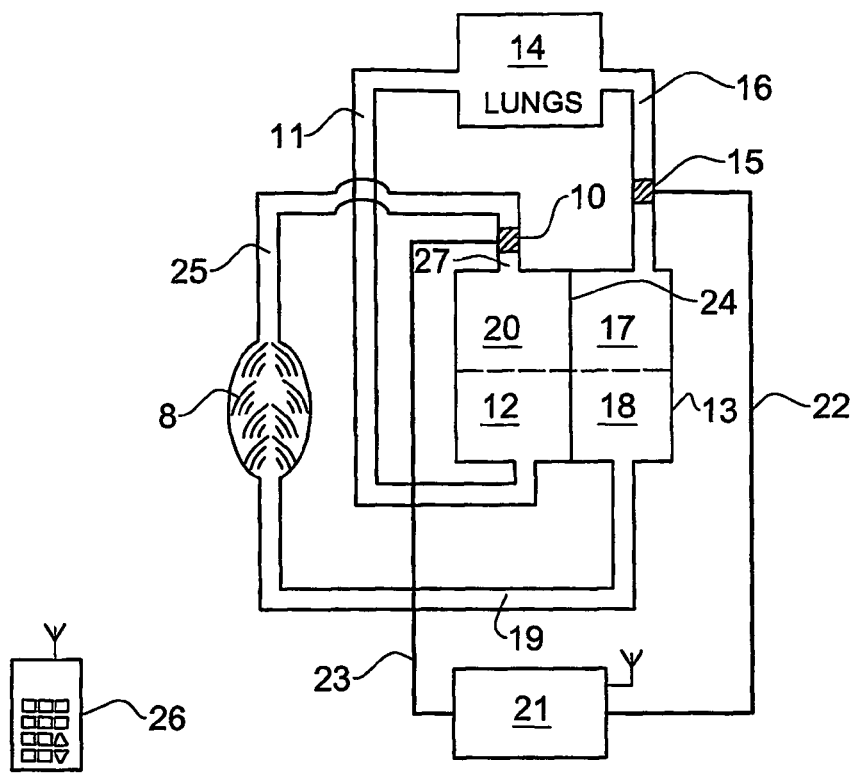
FIGS. 1a to FIG. 1c show a schematic representation of a system in accordance with embodiments of the invention.

FIG. 1a shows schematically a mammalian circulatory system. Oxygen-rich blood passes from the left atrium 17 to the left ventricle 18 before leaving the heart 13 via an arterial system 19 to the body tissues 8. Oxygen-poor blood is delivered from the tissues 8 to the right atrium 20 of the heart 13 by a venous system 25 before passing into the right ventricle 12. The oxygen-poor blood is then delivered to the lungs 14 by the pulmonary arteries 11 before passing into the left atrium 17 by the pulmonary veins 16.

FIG. 1a further shows a system in accordance with one embodiment of the invention. The system comprises a regulator 10, and a monitor 15 for monitoring blood flow rate or blood pressure. In FIG. 1a, the regulator 10 is shown positioned in or adjacent to a vena cava 27 that delivers oxygen-poor blood from the body tissues 8 to the right atrium 20 of the heart 13. The monitor 15 is shown in FIG. 1a positioned near or adjacent to the pulmonary veins 16. The regulator 10 and the monitor 15 can be inserted into the blood vessels by mean of a catheter, or outside the blood vessels by means of an endoscope or catheter through a blood vessel.

The monitor 15 generates signals indicative of a blood flow rate or blood pressure in the pulmonary veins 16 that are transmitted to a controller 21 over a first signal channel 22. The controller 21 includes a processor that is configured to determine from a signal input received from the monitor 15, a blood flow rate or a blood pressure in the pulmonary veins 16. The controller is further configured to determine the cross sectional area in the vena cava 27 that would produce a blood flow rate or blood pressure in the vena cava 27 that is correlated with the desired blood flow or pressure in the pulmonary veins 16. The controller 21 then activates the regulator 10 by means of a second signal channel 23 so that the regulator 10 assumes a conformation that produces the determined cross-sectional area in the vena cava 27.

A micro-controller, such as an Intel 8031/8051 or a Motorola 6000 series, maybe used in the controller 21. However, other micro-controllers such as programmable logic devices (PLD) and gate array logic (GAL) devices may be used. The controller 21 may be programmed to activate the regulator 10 at predetermined times and in selected sequences, at predetermined intensities, or at alternating times and intensities.

The system may optionally include a remote control 26 to allow a patient or health care provider to calibrate the system. Calibration of the system may include, for example, inputting to a memory in the controller 21 parameters of the patient that are required for determining the blood flow rate or blood pressure from the signal output by the monitor 15, or for determining a conformation of the regulator 10 or to achieve a determined blood flow rate or blood pressure in the vena cava 27. These parameters may include, for example, the patient's blood volume, blood pressure, or heart rate at rest and during physical activity. The values of these parameters are input to the processor in the controller 21, for example by the remote control 26.

With the regulator 10 positioned on the vena cava 27 and the monitor 15 positioned on the pulmonary veins 16, the system of the invention may be used in the treatment of congestive heart failure or to prevent nocturnal dyspnea due to a generated increase in the venous return.

Figure 1B:
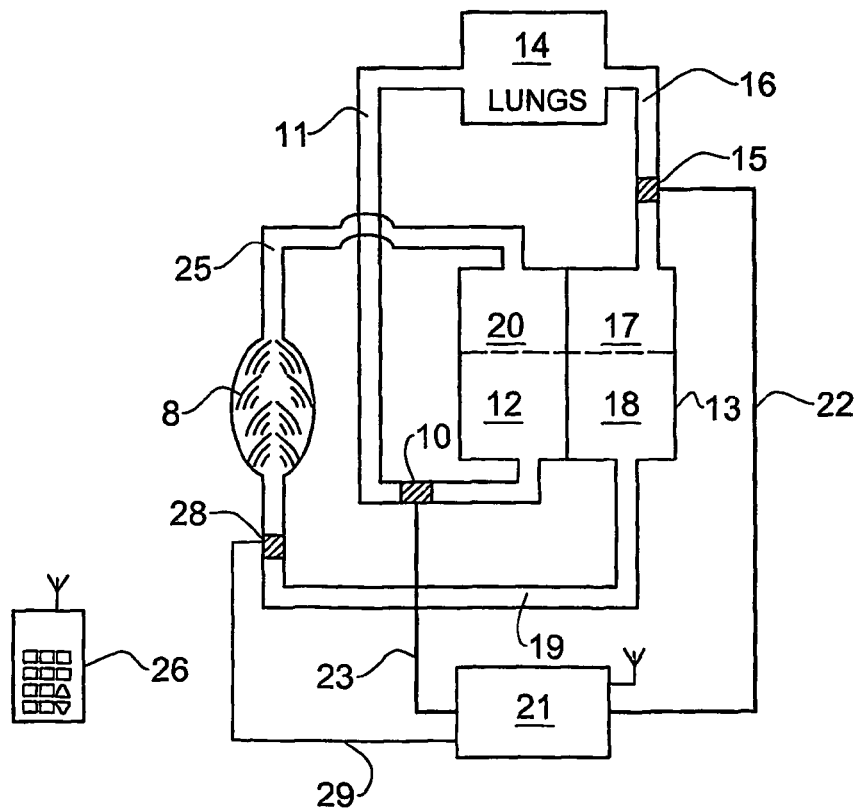

FIG. 1b shows another application of the system of the invention, in which the regulator 10 is positioned on the pulmonary arteries 11 and the monitor 15 positioned on the pulmonary veins 16. In this configuration, the system of the invention may be used in the treatment of pulmonary edema due to left ventricular dysfunction. An alarming sensor 28 may be applied to the arterial system 19. The alarming sensor 28 can be a strain gage that is attached to a wall of a blood vessel of the arterial system 19. The signals of the alarming sensor 28 are transmitted to the controller 21 over the third channel 29. The controller 21 determines the cross sectional area in the pulmonary artery 11 based on the results of the measurements received from the alarming sensor 28 with the data from the monitor 15 and the regulator 10. The controller 21 then activates the regulator 10 by means of the second signal channel 23 50 that the regulator 10 assumes a conformation that produces the determined cross sectional area in the pulmonary artery 11. The controller 21 may be implanted in the body or positioned outside the body. The signal channels 22, 23 and 29 may be, for example, wires. As another example, communication between the processor in the controller 21, the regulator 10, the monitor 15 and the alarming sensor 28 may be via radio or other wireless signals.

Figure 1C:
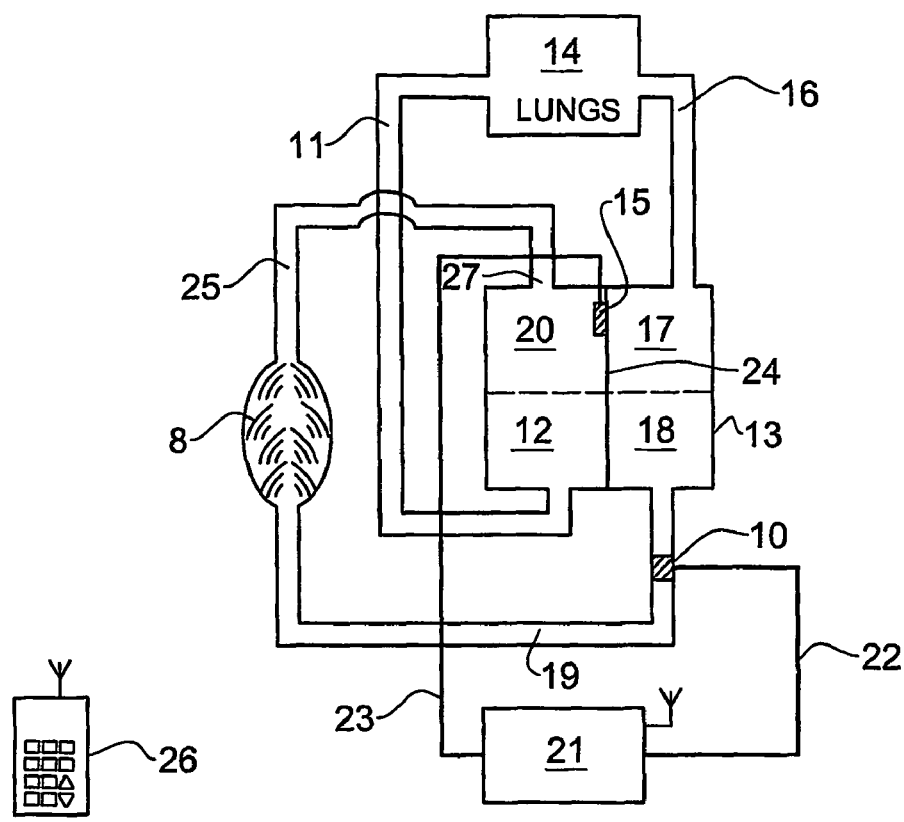

FIG. 1c shows yet another application of the system of the invention, in which the regulator 10 is positioned in the aorta, for example as part of a cardiac assist device, and the monitor 15 is positioned on the interatrial septum 24.

Figure 2:
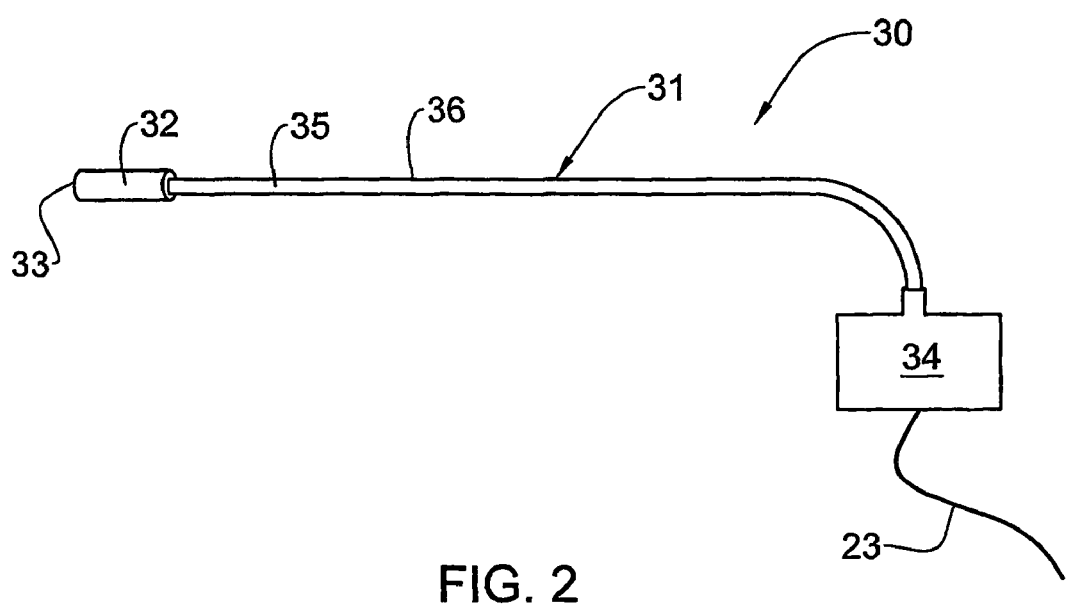
FIG. 2 shows a regulator comprising balloon tipped catheter for use in the system of the invention.

FIG. 2 illustrates a regulator 30 that may be used for the regulator 10 of the system. The regulator 30 includes a balloon catheter having an inflatable balloon 32 at its distal end 33, and a compressor 34. The compressor 34 generates compressed air that is delivered to the balloon 32 via a lumen 35 in the shaft 36 of the regulator 30 so as to inflate the balloon 32. The balloon 32 is shown in its deflated state in FIG. 2. Operation of the compressor 34 is under the control of the controller 21 via the signal channel 23, as described above. In the case that the balloon 32 is deployed into a systemic vein, such as a vena cava 27 or a pulmonary artery 11, and the monitor is deployed in a pulmonary vein 16 and the controller determines that the blood pressure in the pulmonary vein 16 must be lowered to achieve a desired value, the balloon 32 is inflated to decrease the cross-sectional area of the lumen of the systemic vein.

The balloon catheter 31 is introduced into the vascular system by a minimal surgical procedure, for example by a percutaneous intervention procedure through a femoral artery, jugular vein or during a surgical operation. At the end of the procedure the shaft 36 at the proximal end of the balloon catheter 31 is connected to the compressor 34. A compressor 34 may be implanted inside a blood vessel or in the body outside the blood vessel or located outside the body.

Figure 3A:
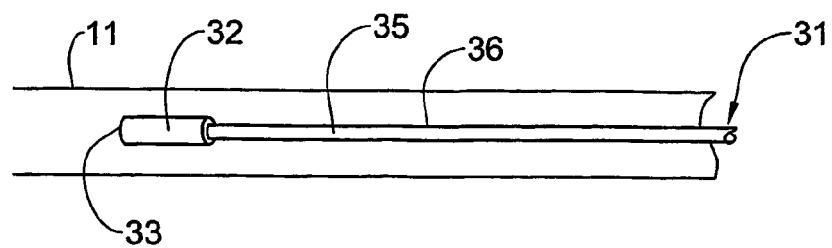
FIG. 3 shows the regulator of FIG. 2 after insertion in a blood vessel.

FIG. 3a shows the distal end 33 of the catheter 31 in the lumen the vena cava 27 or in the lumen of a pulmonary artery 11 with the balloon 32 still in its deflated state.

Figure 3B:
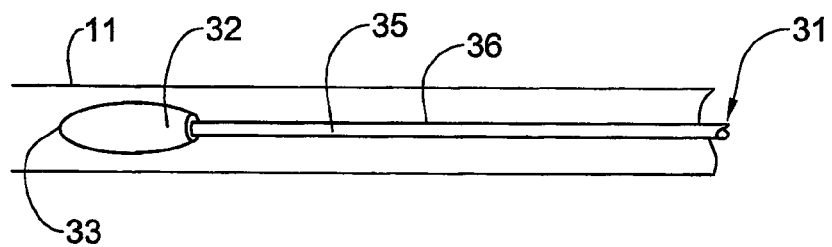

In operation, the controller 21, after processing the signals input from the monitor 15 determines the cross sectional area that would produce a blood flow rate or blood pressure in the vena cava 27 or in the pulmonary artery 11 that generates the desired blood flow rate or blood pressure in the pulmonary vein 16. The controller 21 then activates the compressor that inflates the balloon 32 until the required cross-sectional area of the vena cava 27 or of the pulmonary artery 11 is attained. FIG. 3b shows the balloon inflated to reduce the flow in the vena cava 27 or in the pulmonary arteries 11.

Figure 4A:
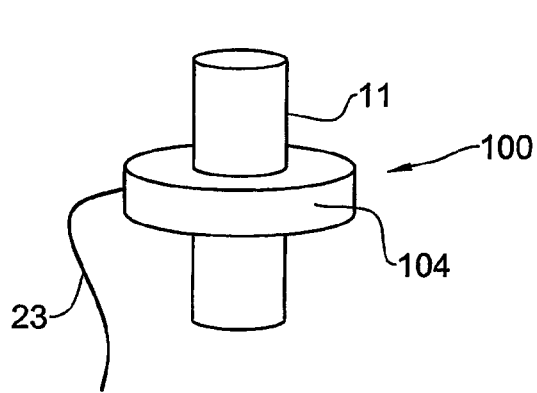
FIG. 4 shows a regulator comprising a ring configured to be secured around a blood vessel.
Figure 4B:
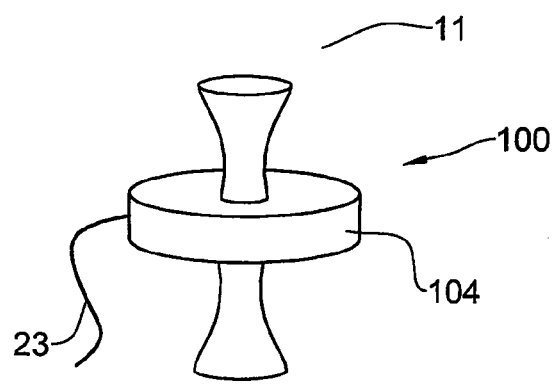

FIG. 4 shows regulator 100 that maybe used for the regulator 10 in the system of the invention. The regulator 100 includes a ring 104 that is dimensioned to partially or completely surround a blood vessel such as the vena cava 27 or the pulmonary arteries 11. The ring is shown in a large caliber conformation in FIG. 4a in which the cross sectional area of the vena cava 27 or the pulmonary arteries 11 is large, and is shown in a low caliber conformation in FIG. 4b in which the cross sectional area of the vena cava 27 or the pulmonary artery 11 is reduced. The caliber of the ring 104 is adjusted under the control of the controller 21 via the signal channel 23, using, for example, the mechanism disclosed in U.S. Pat. No. 5,509,888.

The system may optionally include means to override the actions of the controller 21. For example, the patient or a health care provider may be provided with a control button on the remote control 26 that allows him to determine the conformation of the regulator 10, instead of the processor. The remote control 26 may display measured information regarding the user and the implanted components of the system.

Electrical energy for the controller 21, monitor 15 or the regulator 10 may be provided, for example, by one or more implanted batteries. Alternatively, extra corporal sources of power transmitted via transcutaneous coupling, such as via radio frequency, magnetic flux, photoconduction, or electrical wires may be used.

Some of the components of the system of the invention which in use over contact with body fluids or tissues are made from biocompatible materials. Alternatively, some may be contained in a biocompatible housing. The housing prevents ingress of bodily fluids into the electrical or mechanical mechanisms of the implanted component. Body fluids are extremely corrosive to materials and the housing must be able to withstand chemical attack. The biocompatible materials and housing may be manufactured from any rigid or deformable material, as required. Exemplary biocompatible materials include: titanium or titanium alloys, such as Ti-6A14V; cobalt-based ferrous alloys; nickel alloys, such as nickel-titanium alloys, including NITINOL (which is an alloy of nickel (Ni) and titanium (Ti) developed by the Naval Ordinance Laboratories (NOL) at Silver Spring, Md., USA, commercially available from Raytheon, Menlo Park, Calif., USA); ceramic materials, such as high-density aluminum oxide; carbon compounds such as pyrolytic carbon, vitreous carbon, or vapor deposited carbon on substrates; and plastic materials, such as medical grades of polyethylene, polypropylene, perfluorinated polymers, acrylic polymers, polyurethanes, or silicone rubbers.

The invention claimed is:

1. A system for regulating a blood flow rate or blood pressure to achieve balanced flow rates or blood pressures between a first blood vessel or heart chamber and a second blood vessel or heart chamber, wherein the first blood vessel or heart chamber and the second blood vessel and heart chamber are on opposite sides of the circulatory system, and wherein the first blood pressure or heart chamber is regulated by the system only by a regulator applied to the second blood vessel or heart chamber, the system comprising:

i) a monitor monitoring parameters indicative of a difference between the flow rate or blood pressure of the first blood vessel or heart chamber and the flow rate or blood pressure of the second blood vessel or heart chamber;

ii) the regulator regulating the blood flow rate or blood pressure in at least a portion of the second blood vessel or heart chamber; and iii) a controller configured to:

receive a signal from the monitor;

determine from the signal a difference between the flow rate or blood pressure of the first blood vessel or heart chamber and the flow rate or blood pressure of the second blood vessel or heart chamber;

determine from the difference between the flow rate or blood pressure of the first blood vessel or heart chamber and the flow rate or blood pressure of the second blood vessel or heart chamber a second blood flow rate or blood pressure in the second blood vessel or heart chamber that generates a second blood flow rate or blood pressure in the first blood vessel or heart chamber to yield the balanced flow rate or blood pressure between the first blood vessel or heart chamber and the second blood vessel or heart chamber; and signal the regulator to generate the second determined blood flow rate or blood pressure in the at least portion of the lumen of the second blood vessel or heart chamber.

2. The system according to claim 1 wherein the monitor monitors parameters indicative a blood flow rate or blood pressure in the first blood vessel or heart chamber.

3. The system according to claim 1 wherein the regulator is configured to decrease the blood flow rate or blood pressure in at least a portion of the second blood vessel or heart chamber below a naturally occurring blood flow rate or blood pressure.

4. The system according to claim 3 for the treatment of congestive heart failure or pulmonary edema or nocturnal dyspnea.

5. The system according to claim 1 wherein at least one of the monitor, the regulator and the controller, is an implanted device.

6. The system according to claim 1 wherein communication between the system components is wired or wireless.

7. The system according to claim 1 further comprising a remote control.

8. The system according to claim 1 wherein the controller is configured to be programmed by remote control.

9. A method for regulating a blood flow rate or blood pressure to achieve balanced flow rates or blood pressures between a first blood vessel or heart chamber and a second blood vessel or heart chamber, wherein the first blood vessel or heart chamber and the second blood vessel and heart chamber are on opposite sides of the circulatory system, and wherein the first blood pressure or heart chamber is regulated by the system only by a regulator applied to the second blood vessel or heart chamber, the method comprising:

i) monitoring parameters indicative of a difference between the flow rate or blood pressure of the first blood vessel or heart chamber and the flow rates or blood pressure of the second blood vessel or heart chamber;

ii) determining a difference between the flow rate or blood pressure of the first blood vessel or heart chamber and the flow rate or blood pressure of the second blood vessel or heart chamber from the signal;

iii) determining from the difference between the flow rate or blood pressure of the first blood vessel or heart chamber and the flow rate or blood pressure of the second blood vessel or heart chamber a second blood flow rate or blood pressure in the second blood vessel or heart chamber that generates a second blood flow rate or blood pressure in the first blood vessel or heart chamber to yield the balanced flow rate or blood pressure between the first blood vessel or heart chamber and the second blood vessel or heart chamber; and iv) generating the second determined blood flow rate or blood pressure in the at least portion of the lumen of the second blood vessel or heart chamber.

10. The method according to claim 9 comprising monitoring parameters indicative a blood flow rate or blood pressure in the first blood vessel or heart chamber.

11. The method according to claim 9 comprising decreasing the blood flow rate or blood pressure in at least a portion of the second blood vessel or heart chamber below a naturally occurring blood flow rate or blood pressure.

12. The method according to claim 11 for the treatment of congestive heart failure, pulmonary edema, or nocturnal dyspnea.

13. The method according to claim 9 comprising use of at least one implanted device.

14. The method according to claim 9 comprising wired or wireless communication.

15. The method according to claim 9 comprising remote control communication.

16. The method according to claim 15 comprising use of a remote control to program a controller.

17. Apparatus for regulating a blood flow rate or blood pressure to achieve balanced flow rates or blood pressures between a first blood vessel or heart chamber and a second blood vessel or heart chamber, the first blood vessel or heart chamber and the second blood vessel and heart chamber on opposite sides of the circulatory system, comprising:

a processor capable of:

i) monitoring parameters indicative of a difference between the flow rate or blood pressure of the first blood vessel or heart chamber and the flow rates or blood pressure of the second blood vessel or heart chamber;

ii) determining a difference between the flow rate or blood pressure of the first blood vessel or heart chamber and the flow rate or blood pressure of the second blood vessel or heart chamber from the signal;

iii) determining from the difference between the flow rate or blood pressure of the first blood vessel or heart chamber and the flow rate or blood pressure of the second blood vessel or heart chamber a second blood flow rate or blood pressure in the second blood vessel or heart chamber that generates a second blood flow rate or blood pressure in the first blood vessel or heart chamber to yield the balanced flow rate or blood pressure between the first blood vessel or heart chamber and the second blood vessel or heart chamber; and iv) generating the second determined blood flow rate or blood pressure in the at least portion of the lumen of the second blood vessel or heart chamber below a naturally occurring blood flow rate or blood pressure;

a regulator effecting control of flow rate or blood pressure at the second blood vessel or heart chamber, the method.

18. The apparatus of claim 17, wherein the processor comprises one of a micro-controller, a programmable logic device PLD, and a gate array logic (GAL) device, the processor programmed to activate the regulator at predetermined times and in selected sequences, at predetermined intensities, or at alternating times and intensities.

* * * * *